(12) United States Patent
Bambot

(10) Patent No.: US 11,090,016 B2
(45) Date of Patent: Aug. 17, 2021

(54) APPARATUS AND METHOD FOR DIGITAL SCAN MAMMOGRAPHY

(71) Applicant: Shabbir Bambot, West Hills, CA (US)

(72) Inventor: Shabbir Bambot, West Hills, CA (US)

( * ) Notice: Subject to any disclaimer, the term of this patent is extended or adjusted under 35 U.S.C. 154(b) by 95 days.

(21) Appl. No.: 16/499,956

(22) PCT Filed: Apr. 26, 2018

(86) PCT No.: PCT/US2018/029567
§ 371 (c)(1),
(2) Date: Oct. 1, 2019

(87) PCT Pub. No.: WO2018/204159
PCT Pub. Date: Nov. 8, 2018

(65) Prior Publication Data
US 2020/0297298 A1 Sep. 24, 2020

Related U.S. Application Data

(60) Provisional application No. 62/500,094, filed on May 2, 2017.

(51) Int. Cl.
| | |
|---|---|
| *A61B 6/00* | (2006.01) |
| *A61B 6/04* | (2006.01) |
| *A61B 6/06* | (2006.01) |
| *A61B 6/02* | (2006.01) |

(52) U.S. Cl.
CPC ............. *A61B 6/502* (2013.01); *A61B 6/022* (2013.01); *A61B 6/0435* (2013.01); *A61B 6/0492* (2013.01); *A61B 6/06* (2013.01); *A61B 6/4208* (2013.01); *A61B 6/542* (2013.01); *A61B 6/545* (2013.01); *A61B 2562/0261* (2013.01)

(58) Field of Classification Search
CPC .... A61B 6/00; A61B 6/04; A61B 6/06; A61B 6/502; A61B 6/0435; A61B 6/4208; A61B 6/545; A61B 6/0492; A61B 6/542; A61B 6/02; A61B 6/0414; A61B 2562/0261
See application file for complete search history.

(56) References Cited

PUBLICATIONS

No 1449 forms nor any references have been submitted by the Applicants.*

* cited by examiner

*Primary Examiner* — Jurie Yun

(57) ABSTRACT

To improve breast mammography imagery via use of a digital "slot scanning" imaging system that accommodates the changing thickness of the breast from the chest wall to the nipple by scanning the breast from the chest outward to the nipple or vice versa instead of the side-to-side methodology and using Automatic Exposure Control or AEC parameters optimized for the changing thickness and composition of the breast at each scan location and an improved breast compression device, wherein uniform breast compression mechanism includes a first breast plate and a second breast plate, wherein at least one of said first breast plate and said second breast plates includes an angle adjustment or tilt to account for the high variability in breast sizes and configurations while maintaining optimal immobilization with excellent patient comfort.

16 Claims, 2 Drawing Sheets

PRIOR ART  PRIOR ART  PRIOR ART

APPARATUS AND METHOD FOR DIGITAL SCAN MAMMOGRAPHY

This application is a U.S. National Stage Filing under 35 U.S.C. 371 from International Application No. PCT/US2018/029567, filed on Apr. 26, 2018 and published as WO2018/204159, which claims priority to and the benefit of U.S. Provisional Application Ser. No. 62/500,094, filed on May 2, 2017.

BACKGROUND

The invention generally relates to mammography.

Mammography is considered to be one of the most demanding and challenging applications of radiographic medical imaging. The resolution of mammography systems, compared to other radiographic medical applications, must be high in order to detect the earliest lesions and/or masses and must be capable of obtaining images with a resolution on the order of fifty microns or better in order to do so. Contrast requirements are similarly demanding since the differences in radio-opacities between potential cancer and surrounding "healthy" tissue are quite subtle. Mammography is also a procedure that is generally disliked by patients who while acknowledging its benefits often avoid it because of the discomfort and pain from breast compression necessary to get good images. Methods and mechanisms that can help alleviate this discomfort and pain are therefore highly desirable in order to improve patient compliance with mammography testing recommendations.

Resolution and Contrast.

Most mammography systems in use today are known as Full Field Digital Mammography or FFDM systems. These systems use a cone beam of X-rays to radiate the entire breast and a flat, Two Dimensional (2D) detector panel to image the transmitted radiation. This transmitted radiation consists of two types of X-ray photons, primary and scattered. Primary photons are those whose trajectory is not changed upon passing through tissue but their number may be attenuated by features in the tissue. This attenuation shows up as brighter areas on the captured X-ray image and is of diagnostic importance. The scattered photons trajectories are significantly altered upon passing through tissue. They impinge on the detector from a path outside a "direct" or substantially straight path from the radiation source to the detector. These photons do not provide any diagnostic benefit and on the contrary cause random noise and other artifacts in the image. Accordingly, mammographic images should ideally be generated "scatter-free".

Problem with Scatter.

Various attempts have been made at reducing the incidence of scatter in radiographic imaging. For instance, anti-scatter grids consisting of a series of parallel strips of lead placed between the patient and the detector during the exposure are used in FFDM systems to reduce the amount of scatter. Primary photons pass through between the strips as they travel roughly parallel to them, but scattered photons which have, by definition, deviated from the parallel or direct path, cannot easily pass through the grid as they encounter the lead strips at an angle, and are therefore removed from the beam. However, use of these grids generally coincides with a need for significant increase in tissue radiation to make up for the lost radiation in order to generate images of desired resolution, signal-to-noise ratio and/or contrast.

Flat Compression of the Breast.

Mammography requires vigorous breast compression for many reasons. These include holding the breast still and motionless during the measurement in order to reduce blurring artifact, to hold the breast away from the chest wall so that the entire breast tissue along with a small portion of the chest muscle is imaged, a requirement of mammography adequacy and to minimize X-ray radiation dosage. Clearly, the thinner you can make anything you're X-raying the lower the dose that you'll need to use, so by thinning the breast we can use a lower X-ray dose. However, in order to get a more uniform image over the entire breast, it is made to conform to a constant thickness (flat compression) by squeezing the breast between two parallel surfaces or plates called paddles. During a screening procedure, mammography systems capture an X-ray image of the entire breast at once. In other words both the posterior or back portion of the breast (at the chest wall) as well as the anterior or front portion of the breast (at the nipple) are irradiated and imaged at the same time. If the breast is not flattened to a constant thickness then radiation passing through the thicker posterior of the breast will cause the image to be under-exposed. On the other hand, if sufficient radiation is used so that the posterior is properly exposed or in other words, well-penetrated by X-rays so that the details can be seen then the anterior of the breast will be over-exposed since there will be too much X-ray that gets through. So the compression is used to reduce and equalize the thickness, making its thickness constant or flat so that the image is more easily interpreted.

Breasts, however, are cone shaped with the posterior portion being larger than the anterior. With flat compression, the posterior part of the breast is compressed too much and often uncomfortable or painful and cause bruising while the anterior part of the breast may not be compressed at all. It is therefore desirable to make a measurement by alleviating the pain and discomfort of breast compression to achieve better compliance with mammography recommendations.

SUMMARY OF THE INVENTION

Provided herein are systems, methods and apparatuses for Digital Scan Mammography.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

Figures 1A, 1B, 1C:
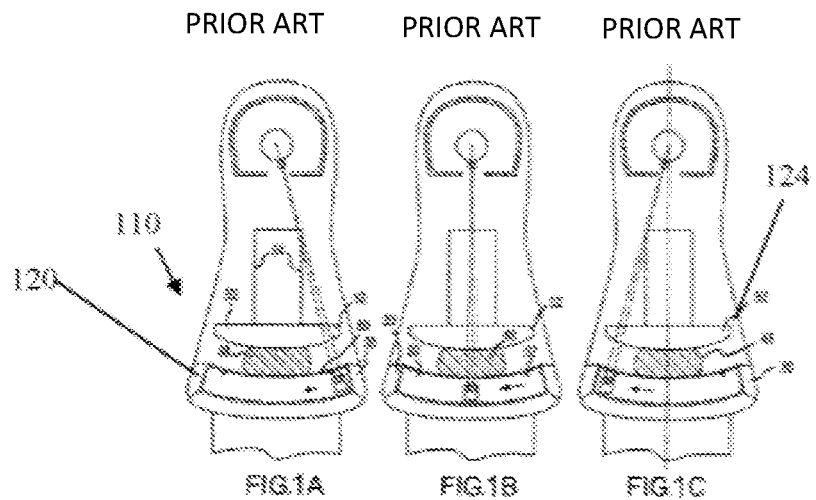
FIGS. 1A-C is a schematic of a scanning configuration used in prior art. The beam is scanned in concert with the detector from side to side i.e. from medial to lateral position with respect to the patient or vice versa while the breast is held compressed between two curved but essentially parallel plates.
Figure 2:
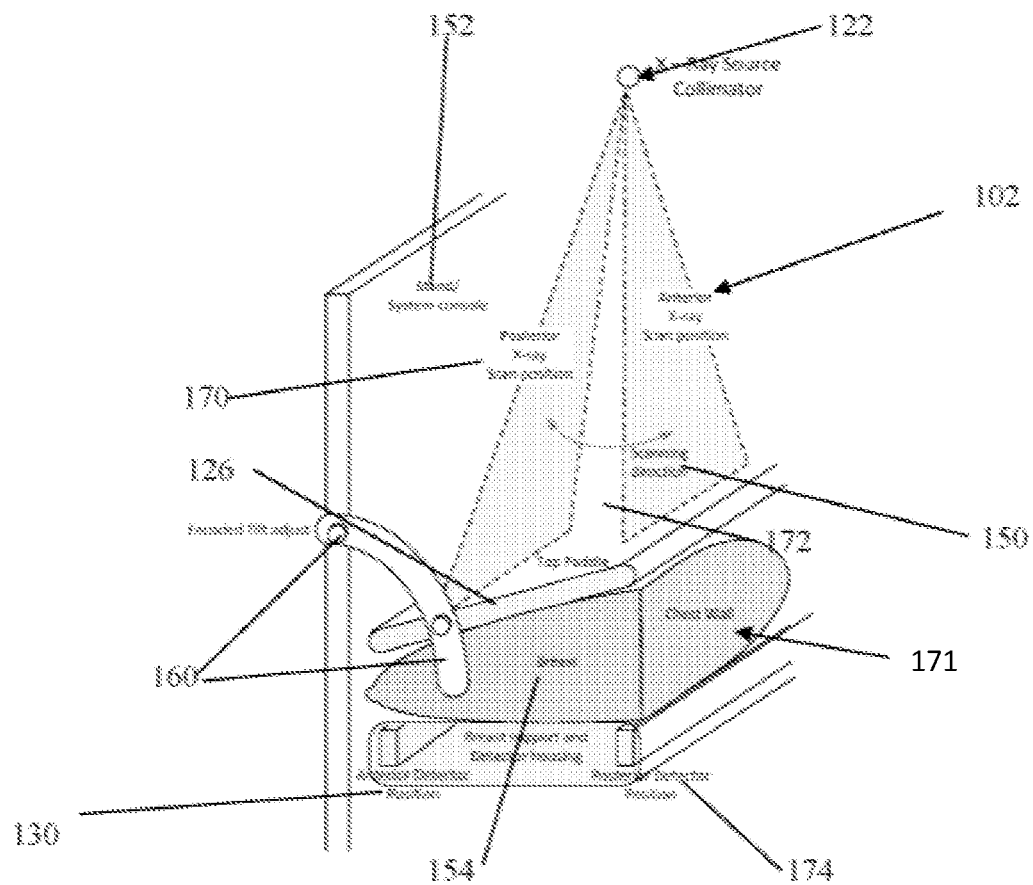
FIG. 2 is a schematic of a scanning configuration according to one embodiment. The beam is scanned in concert with the detector from front to back i.e. from anterior to posterior position with respect to the patient or vice versa while the breast is held compressed between the top paddle and the breast support one or both of which can be tilted to accommodate the generally conical shape of the breast.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words anterior and posterior are applied herein with respect to the patient (Anterior refers to the nipple portion of the patient. Posterior refers to the chest wall with respect to a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The present invention is directed to a radiographic imaging device and associated method for reducing effects related to scattered radiation or scatter and to obtain improved imaging performance. Relatedly, the present invention is also directed to help improve compliance with mammography recommendations by reducing the pain and discomfort from breast compression during a mammography examination.

In mammography, reducing the effects related to scatter can improve the contrast (for given imaging parameters) of features being imaged such as lesions, masses, calcifications and the like. Such scatter effects are reduced according to the present invention by reducing detected or recorded scatter as is explained in the following paragraphs. This imaging improvement may allow for various additional advantages including, but not limited to, reduced patient dosages, improved resolution and better overall outcomes.

One advance in digital imaging systems is "slot scanning" which uses a narrow, tightly collimated X-ray beam that scans the tissue while being in precise alignment with a narrow slotted image detector that is operated in Time Delay Integration (TDI) mode. This technique is described in detail in U.S. Pat. No. 5,526,394, which is incorporated herein in its entirety by reference. To image the full area of interest, the narrow, highly collimated, X-ray beam to scan the tissue in precise alignment with a slotted (line shaped) detector and a composite image of the full area of interest is constructed from the incrementally obtained information. In doing so, significant scatter rejection is achieved because radiation outside of the plane (or narrow wedge 172) including the signal source and the active detector area is not recorded as part of the image forming information. In TDI, the scan speed is exactly matched to the speed at which signal is read off a detector to produce the incrementally constructed image. The scanned TDI approach provides significant advantages including, but not limited to, reducing the effects of scattered radiation, providing for full field breast imaging and reducing the required radiation dosage. As will be discussed in the ensuing, slot scanning also enables reducing the pain and discomfort from breast compression during a mammography examination.

An important aspect of any FFDM system is Automatic Exposure Control or AEC. AEC algorithms optimize and select, without any user intervention, parameters (commonly known as technique) such as the peak kilovoltage (kVp), the current used (milli Amperes or mAs), the exposure duration and the target/filter combination for the X-ray measurement for a given breast thickness and density. The goal of the AEC is to produce an image with optimal and uniform Signal to Noise Ratio (SNR) and Contrast to Noise Ratio (CNR) throughout the image. In most FFDM systems a brief exposure (often referred to as a pre-exposure) is used to determine these parameters which are frequently different, for example, between the CC and MLO (Cranio Caudal and Medio Lateral Oblique) views on the same patient. However, AEC parameters are required by design to be constant over the entirety of each image in FFDM systems.

Scanning systems require a different implementation of AEC. Since "Slot scanning" technology builds an image incrementally it provides an opportunity to vary AEC parameters within each image. Dynamic modulation of AEC parameters has been explored in the prior art. For example, Aslund, M and colleagues [AEC for scanning digital mammography based on variation of scan velocity. Med Phys. 2005 November; 32(11): 3367-74 which is incorporated herein in its entirety by reference] explored a velocity-modulation approach for a photon-counting scanning detector. In their approach, the detector-beam velocity changes during the clinical scan, based on photon count rates, in order to achieve an optimal signal to noise ratio throughout the image.

An apparatus and method for improved digital mammography comprises using "slot scanning" that accommodates uniform force or pressure in breast compression to make it less painful and more comfortable for the patient. "Uniform compression" is herein defined as a mostly even force or pressure applied at all points ranging between the anterior and posterior part of the breast. The compressive force applied in mammography can range from about 50 to about 200 Newton (about 10 to about 45 lb/f (about 50 to about 200 Newton) that can result in a pressure within the breast tissue of about 0.5 to about 5 psi depending upon the size and volume of breast tissue.

In one embodiment, the apparatus and method for improved digital mammography comprises accommodating the conical shape of the breast with compression between plates that have an adjustable mutual tilt 160, which allows for a more uniform force or pressure (uniform compression) to be applied to the breast 154. In one example the adjustable mutual tilt couples to a stand 152. The cone shape of the breast is more comfortably accommodated when the separation between the plates is allowed to be larger near the chest wall 171 and smaller near the nipple. The uniform compression also reduces image artifacts that may arise from over-compression in some parts of the breast and under-compression in others.

In one embodiment, uniform compression force between plates with an adjustable mutual tilt helps hold the breast still and motionless and away from the chest wall so that the entire breast tissue along with a small portion of the chest muscle is imaged.

In another embodiment, the bottom plate is held at right angles to the vertical and the breast is rested upon this bottom plate while the top plate has an adjustable angle or tilt that the technician can then place to provide uniform compression on the breast. This adjustability will produce a natural tilt in the top plate and will account for the high variability in breast sizes and configurations while maintaining optimal immobilization with excellent patient comfort. This degree of tilt is manually recorded or is recognized by sensors and this information is used to determine the changing thickness of the breast from the chest wall to the nipple.

In an alternate embodiment, no compression is applied allowing the breast to simple rest on the breast support and the breast assume its natural conical shape.

In one embodiment, the apparatus and method for improved digital mammography comprises using "slot scanning" with uniform force or pressure in breast compression by adopting a scanning methodology in which the narrow X-ray beam and the narrow slotted image detector are scanned in a direction that is essentially orthogonal to and thereby different from the side-to-side scanning methodology taught by the prior art including U.S. Pat. No. 5,526,394 (cited above). Indeed U.S. Pat. No. 5,526,394 teaches away from the present invention by stating: "Movement of the receiver is preferably performed across the patient's chest (from side-to-side relative to the patient's breast) rather than transverse to the patient's chest wall (outward from the base of the patient's breast or vice versa) so that the scan is not interrupted by the chest wall, thereby facilitating a smooth scanning motion across the entire breast for enhanced imaging." In one embodiment, current FFDM systems can also use uniform (non flat) compression but because they use cone beam radiation (which provides the same radiation over the entire breast) the thicker posterior of the breast may cause the image to be under-exposed and the thinner anterior may cause the image to be over-exposed.

Since the breast is cone shaped its thickness changes substantially from the posterior (chest wall) to the anterior (nipple) and this change in thickness is much more so than any change in thickness going from side to side (medial to lateral). Therefore this alternative scanning method scans over tissue of changing thickness.

In one embodiment the apparatus and method for improved digital mammography comprises using "slot scanning" with uniform force or pressure in breast compression by changing the AEC parameters to the most optimum valued depending upon the thickness of the breast tissue and optionally its other physical properties, such as glandularity at the scan position 102. This embodiment enables comfortable uniform compression.

In one embodiment, the thickness information is provided to the AEC processor for calculating the AEC parameters prior to making the measurement. The thickness may be between about 2 to about 20 cm. This permits changes in the AEC parameters from one scan position 150 to the next 170. For example, the AEC parameters such as kVp and mAs can be different for scan measurements near the chest wall as compared to the measurements near the nipple thereby providing for optimal and uniform S over the entire image. In general, doubling the tissue thickness reduces the penetration (P) by the square of the increase in thickness. The half value layer (HVL) thickness is defined as the thickness of material that reduces the radiation by about 50%. So for example if we choose double the HVL thickness the penetration $P=(0.5)2=0.25$. The HVL thickness for tissue depends upon the type of tissue such as fatty, glandular, muscle etc. as well as the kVp and mAs used. Increasing the kVp increases the HVL thickness as does increasing mAs.

In an alternate embodiment, both top and bottom plates are provided with an adjustable tilt. It is understood that in scanning the breast from the chest wall to the nipple, the scanning beam may not be exactly parallel to the chest wall and small variations in the angle (from about 0° up to about 30°) between the chest wall and scan beam may be used to accommodate patient anatomy and patient positioning.

Notwithstanding the above, an alternative embodiment may use a narrow slotted image detector that is composed of multiple sections each section of which can be independently addressed to provide for different detector related AEC parameters. In this case, side to side (i.e. medial to lateral) scanning can be used but the detector section near the chest wall will use AEC parameters that accommodate thicker tissue as compared to the detector section near the nipple.

A related aspect of the apparatus and method for improved digital mammography is to use surface features on the compressing plates that help them to "grab" onto the skin for better immobilization. Such features include surface texture, surface elasticity, protrusions or holes that have the effect of providing sufficient friction or holding capacity to prevent slippage during a measurement. Surface elasticity may add to capability of holding the breast in position. Additionally, such features can have subtle radio markers or patterns that may be useful as fiduciary markers in an image. When holes are used they may also be used as access ports for biopsy.

Another aspect of the apparatus and method for improved digital mammography is to use a strain gauge to determine the extent of compressive force being applied on the breast. Since this force is uniform it is expected that a single force value can be used to determine if the breast of a particular patient is over or under compressed thereby allowing for a standardization of compressive force that may vary based on patient age, menopausal stage, demographics and other related factors.

In one embodiment, a pre-measurement is made at one or more select positions on the immobilized breast prior to actual imaging by slot scanning. For example, this pre-measurement may be made at 3 positions, one near the chest wall, one near the nipple and one in between and these measurements can be used to approximate the tissue composition and density among other features that are commonly measured in mammography pre-measurements. In another embodiment, the pre-measurements may be made between about 1 and about 10 positions. The data from this pre-measurement are used as inputs into the AEC algorithm for determining the best AEC parameters for that patient.

A separate aspect of the apparatus and method for improved digital mammography is to use flat plates or paddles as opposed to curved plates or paddles for holding and compressing the breast. Scanning systems such as the one described in the U.S. Pat. No. 5,526,394 have compression paddles that have a curved shape to facilitate the curved trajectory of the detector's movement whilst the detector's surface is always held at right angles to the X-ray beam.

However, curved paddles are difficult to use in special imaging modes often used in mammography such as such as enlargement and spot imaging. It is also difficult to accommodate existing biopsy devices designed for flat paddles for use in curved paddles. To address this problem U.S. Pat. No. 7,590,217 (which is incorporated herein in its entirety by reference) teaches using an essentially flat upper and lower compression paddles and a sensor that is kept in synch with the scanning movement of the X-ray beam by moving it along a linear path but tilting its active surface as necessary to keep the surface essentially at right angles to the X-ray beam. This scheme is expected to eliminate or reduce the variability in detector collection efficiency at the edges of the scanning range when compared to the middle. This method however introduces additional system cost and complexity and the variability that it attempts to remove can easily be removed by appropriate calibration.

In one embodiment, the apparatus and method for improved digital mammography uses flat paddles and a sensor located below the bottom paddle that does not tilt in its linear movement between the extremes of the scanning movement. In this regard the measurement is similar to the measurement that would have been obtained by using a flat 2D detector such as the ones used in conventional FFDM systems. If necessary, a simple calibration correction such as multiplying the measured values by a set of efficiency factors obtained by measuring a flat acrylic calibration target will correct for variability in efficiency between different scan positions of the detector.

An optional aspect of this invention is to limit radiation to only the area occupied by the patient's breast by first determining the area of contact of the breast on one or both paddles using a method such as contact capacitance, resistance, heat, or similar. The contact surface measuring capability can be built into the paddle itself or onto a pad that determines this area and which can be removed, without disturbing the breast positioning, before the measurement starts.

Yet another aspect of the apparatus and method for improved digital mammography is that it can use more than one detector in order to make a faster measurement. For example two detectors may be used in tandem where one detector travels from the middle to the anterior end while the other travels from the posterior end to the middle. Clearly two spatially separated fan beams are needed for this scheme, one for each detector and these beams can be obtained from the same X-ray tube using spatially separated apertures on the collimator assembly.

It is also clear that while the present invention is described in the context of standard two shot mammography (CC and MLO) imaging, as is commonly practiced, it can easily be extended to other views including Medio Lateral (ML) and reverse CC etc. The apparatus and method for improved digital mammography can also be used for capturing multiple angular views as are captured in Digital Breast Tomosynthesis or DBT for generating a Three Dimensional or 3D view of the breast. Adoption of DBT has been steadily increasing with increasing evidence of its value in reducing false positives and increasing detection of smaller cancers and lesions. The present invention therefore provides the same benefits to DBT as it does to standard screening mammography.

Figure 3:
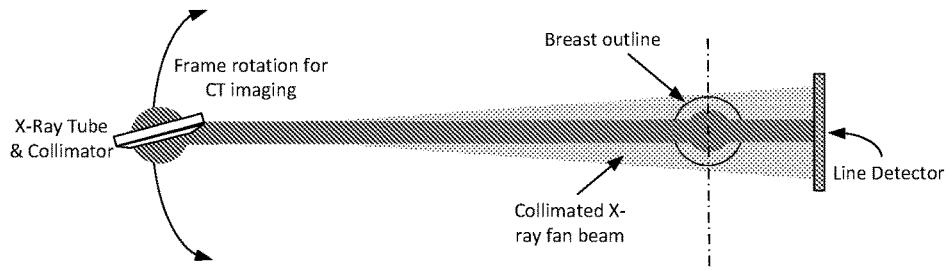
FIG. 3 is a schematic diagram of a system for changing the thickness and composition of the breast while scanning from the chest wall to the nipple and where slot scanning of the pendant breast of a prone patient is performed.
Figure 3:
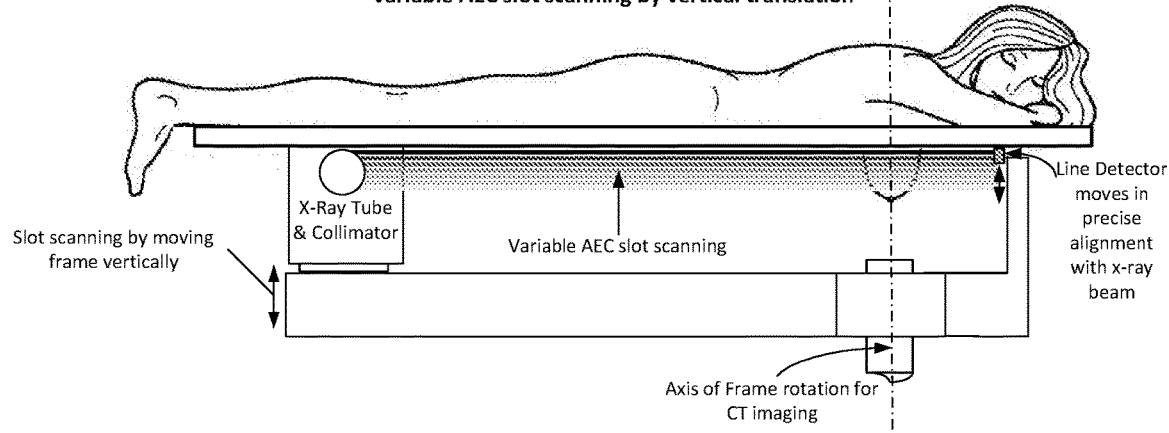
Figure 3:
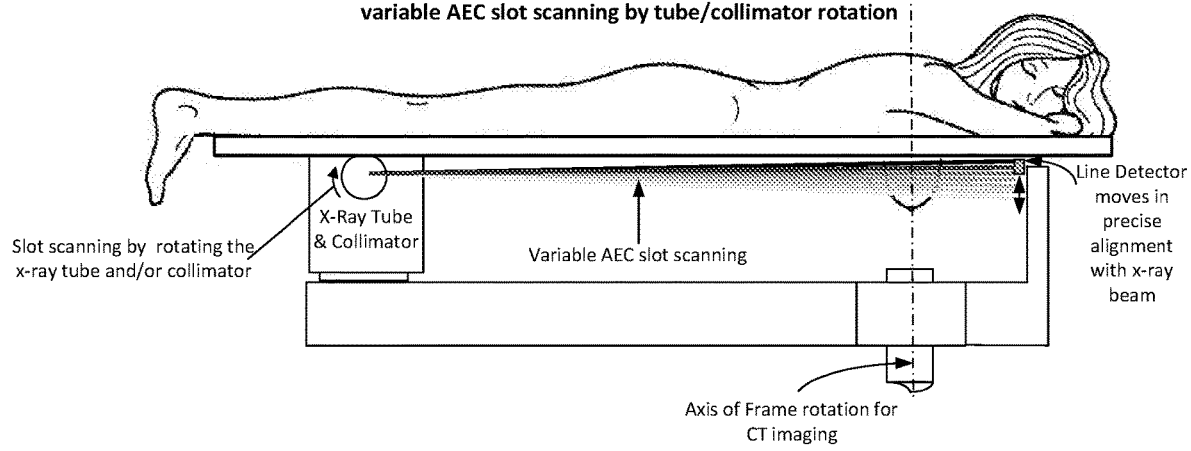

Finally, aspects of this invention may also be used in 3D Computed Tomography (3D CT) imaging such as imaging of the breast as described in U.S. Pat. No. 9,636,072 Computed Tomography Breast Imaging and Biopsy System [incorporated herein in its entirety by reference]. Although, in this system the uncompressed breast is measured, a better more accurate measurement can be made by using AEC parameters that are optimized to the changing thickness and composition of the breast while scanning from the chest wall to the nipple. Such a system is illustrated in FIG. 3 where slot scanning of the pendant breast of a prone patient is performed. The scanning function is achieved by either vertically translating the X-ray beam or rotating it in order to scan the patient's breast whilst a line shaped detector is held in precise alignment with scanning the X-ray beam. CT capability can be additionally provided by rotating the arm holding the X-ray tube and detector so as to capture images from multiple angles around the pendant breast. Image reconstruction can be performed using methods described in U.S. Pat. No. 9,636,072 and the images produced can be viewed using volumetric information visualization methods such as in multi planar reformatted (MPR) mode where images can be reviewed in axial, sagittal, and coronal planes and/or in a volume rendered views similar to conventional CT viewing methods.

The present embodiments may be incorporated as components into a system or software. A general purpose computing device in the form of a computing environment, including a processing unit, a system memory, and display. A system bus may couple various system components of the computing environment, including the processing unit, the system memory, and the display. The processing unit may perform arithmetic, logic and/or control operations by accessing system memory. For example, the processing unit may control the various system components to acquire data for imaging and may process the acquired data to generate an image. Alternatively, different system processors, or different devices including, for example, graphical processing units (GPUs) may control the various system components to acquire data for imaging and may process the acquired data to generate an image.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Software includes applications and algorithms. Software may be implemented in a smart phone, tablet, or personal computer, in the cloud, on a wearable device, or other computing or processing device. Software may include logs, journals, tables, games, recordings, communications, SMS messages, Web sites, charts, interactive tools, social networks, VOIP (Voice Over Internet Protocol), e-mails, and videos.

In some embodiments, some or all of the functions or process(es) described herein and performed by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A breast imaging system, comprising:
   a narrow slotted image detector;
   a scanning mechanism comprising an X-ray source operable to generate a tightly collimated line-shaped X-ray beam, wherein the line-shaped X-ray beam is precisely aligned with the narrow slotted image detector;
   wherein the scanning mechanism is operable to scan breast tissue of a breast along a direction that is substantially orthogonal to a chest wall of a patient; and
   wherein at least two different sets of Automatic Exposure Control (AEC) parameters are used by the image detector to obtain scan measurements on the breast.

2. The system of claim 1, wherein the image detector is operated in a time delay integration (TDI) mode.

3. The system of claim 1, wherein the breast is held between a first breast plate and a second breast plate, wherein at least one of the first breast plate and the second breast plate includes an angle adjustment mechanism or a tilt mechanism adjustable to apply a substantially uniform compression force to the breast.

4. The system of claim 3, wherein at least one of the first breast plate and the second breast plate includes a surface feature for immobilizing the breast, the surface feature comprising a surface texture, a surface elasticity, a plurality of protrusions or a plurality of holes.

5. The system of claim 3, wherein at least one of the first breast plate and the second breast plate includes a plurality of radio markers or radio patterns thereon.

6. The system of claim 3, further comprising a strain gauge to determine an extent of compressive force being applied on the breast.

7. The system of claim 1, further comprising flat paddles, at least one paddle including one or more sensors operable to determine an area of contact of the breast on at least one of the paddles using a contact capacitance-based method, a resistance-based method, or a heat-based method.

8. A method for imaging breast tissue of a breast, the method comprising the steps of:
   precisely aligning a narrow slotted image detector with a tightly collimated line-shaped X-ray beam generated by an X-ray source;
   performing at least a first scan measurement along a first breast segment of the breast by scanning the first breast segment along a direction that is orthogonal to a chest wall of a patient using a first Automatic Exposure Control (AEC) parameter of the image detector;
   performing at least a second scan measurement along a second breast segment of the breast by scanning the second breast segment along a direction that is orthogonal to the chest wall of the patient using a second AEC parameter of the image detector, wherein the second AEC parameter is different from the first AEC parameter.

9. The method of claim 8, further comprising operating the image detector in time delay integration (TDI) mode.

10. The method of claim 8, further comprising holding the breast between a first breast plate and a second breast plate, and adjusting an angle adjustment mechanism or a tilt mechanism to apply a substantially uniform compression force to the breast.

11. The method of claim 10, wherein the holding further comprises immobilizing the breast with a surface feature on at least one of the first breast plate and the second breast plate, the surface feature comprising a surface texture, a surface elasticity, a plurality of protrusions or a plurality of holes.

12. The method of claim 10, at least one of the first breast plate and the second breast plate includes a plurality of radio markers or radio patterns thereon.

13. The method of claim 10, further comprising determining an extent of the compression force applied on the breast.

14. The method of claim 8, further comprising determining an area of contact of the breast on at least one paddle of a plurality of flat paddles using at least one sensor and a contact capacitance-based method, a resistance-based method, or a heat-based method.

15. The method of claim 8, further comprising, prior to the performing, obtaining one or more pre-measurements of each of the first breast segment and the second breast segment using limited X-ray exposure to determine at least one corresponding physical parameter of the breast tissue.

16. The method of claim 15, further comprising, based on the obtaining, determining the first and second AEC parameters for the image detector.

* * * * *